United States Patent
Bertoni

(10) Patent No.: US 10,260,037 B2
(45) Date of Patent: Apr. 16, 2019

(54) SYSTEM AND METHOD TO DIVIDE LIPOSUCTION FAT INTO ALIQUOTS

(71) Applicant: Biomed Device S.R.L., Reggello (FI) (IT)

(72) Inventor: Marco Bertoni, Reggello (IT)

(73) Assignee: Biomed Device S.R.L., Modena (MO), Fraz, Cognento (IT)

( * ) Notice: Subject to any disclaimer, the term of this patent is extended or adjusted under 35 U.S.C. 154(b) by 370 days.

(21) Appl. No.: 14/909,532

(22) PCT Filed: Aug. 1, 2014

(86) PCT No.: PCT/IB2014/063634
§ 371 (c)(1),
(2) Date: Feb. 2, 2016

(87) PCT Pub. No.: WO2015/015471
PCT Pub. Date: Feb. 5, 2015

(65) Prior Publication Data
US 2016/0186125 A1    Jun. 30, 2016

(30) Foreign Application Priority Data

Aug. 2, 2013  (IT) ............................. MO2013A0227

(51) Int. Cl.
*A61M 1/00* (2006.01)
*C12M 1/00* (2006.01)
(Continued)

(52) U.S. Cl.
CPC .......... *C12M 47/04* (2013.01); *A61M 1/0209* (2013.01); *C12M 33/04* (2013.01);
(Continued)

(58) Field of Classification Search
CPC . A01N 1/0257; A01N 1/0284; A61M 1/0209; A61M 1/0272; A61M 1/3695; A61M 2202/08
See application file for complete search history.

(56) References Cited

U.S. PATENT DOCUMENTS 8,361,042 B1 * 1/2013 Gonzalez ............ A61M 1/0001
604/317
2006/0064070 A1 * 3/2006 Martin ................ A61M 1/0281
604/403
(Continued)

FOREIGN PATENT DOCUMENTS

WO  WO 2006/029270   3/2006
WO  WO 2006/100651   9/2006
(Continued)

OTHER PUBLICATIONS

International Search Report and the Written Opinion dated Jun. 8, 2015 From the International Searching Authority Re. Application No. PCT/IB2014/063634 and Its Translation Into English.

*Primary Examiner* — Benjamin Klein

(57) ABSTRACT

A system (1) to divide liposuction fat into aliquots, comprising taking means (2, 3) to take from a container a quantity of adipose material, made available by means of liposuction, and to preserve sealed the quantity taken, the system (1) also comprising at least a separation syringe (4) able to be put in communication with said taking means (2, 3), and able to contain at least a portion of said quantity, the separation syringe (4) being provided so as to separate, by gravity, the fat from the aqueous fluids composing the adipose material, first connection means (5) to put in sealed communication the taking means (2, 3) with the separation syringe (4), at least a rejection container (6), able to be put in communication with the separation syringe (4) so as to receive the aqueous fluids, following their ejection from the
(Continued)

separation syringe (4), at least a syringe device (7, 8) able to be put in sealed communication with the separation syringe (4) so as to receive an aliquot of fat, following its ejection from the separation syringe (4), the syringe device (7, 8) being able to contain sealed and to inject fat to make infiltrations, and second connection means (9) able to put in sealed communication alternately the separation syringe (4) and the rejection container (6) or the separation syringe (4) and the syringe device (7, 8), where the syringe device (7, 8) comprises at least a receptacle (7) and at least an infiltration syringe (8), connected sealed to one another, and is connectable in a removable manner to the second connection means (9) to define, as a result of their filling with fat, a portable unit to contain and to inject an aliquot of fat.

10 Claims, 1 Drawing Sheet

(51) Int. Cl.
*A61M 1/02* (2006.01)
*C12M 1/26* (2006.01)
*C12M 1/12* (2006.01)
*C12N 5/077* (2010.01)
*A61M 1/36* (2006.01)

(52) U.S. Cl.
CPC ............ *C12M 37/04* (2013.01); *C12M 47/00* (2013.01); *C12N 5/0653* (2013.01); *A61M 1/3695* (2014.02); *A61M 2202/08* (2013.01)

(56) References Cited

U.S. PATENT DOCUMENTS

2008/0154240 A1* 6/2008 Shippert ............. A61M 1/0001
604/542
2008/0171951 A1* 7/2008 Fell ..................... A61M 1/3693
600/573
2012/0276628 A1* 11/2012 Khan .................... C12M 45/09
435/378

FOREIGN PATENT DOCUMENTS

WO    WO 2013/111130    8/2013
WO    WO 2015/015471    2/2015

* cited by examiner

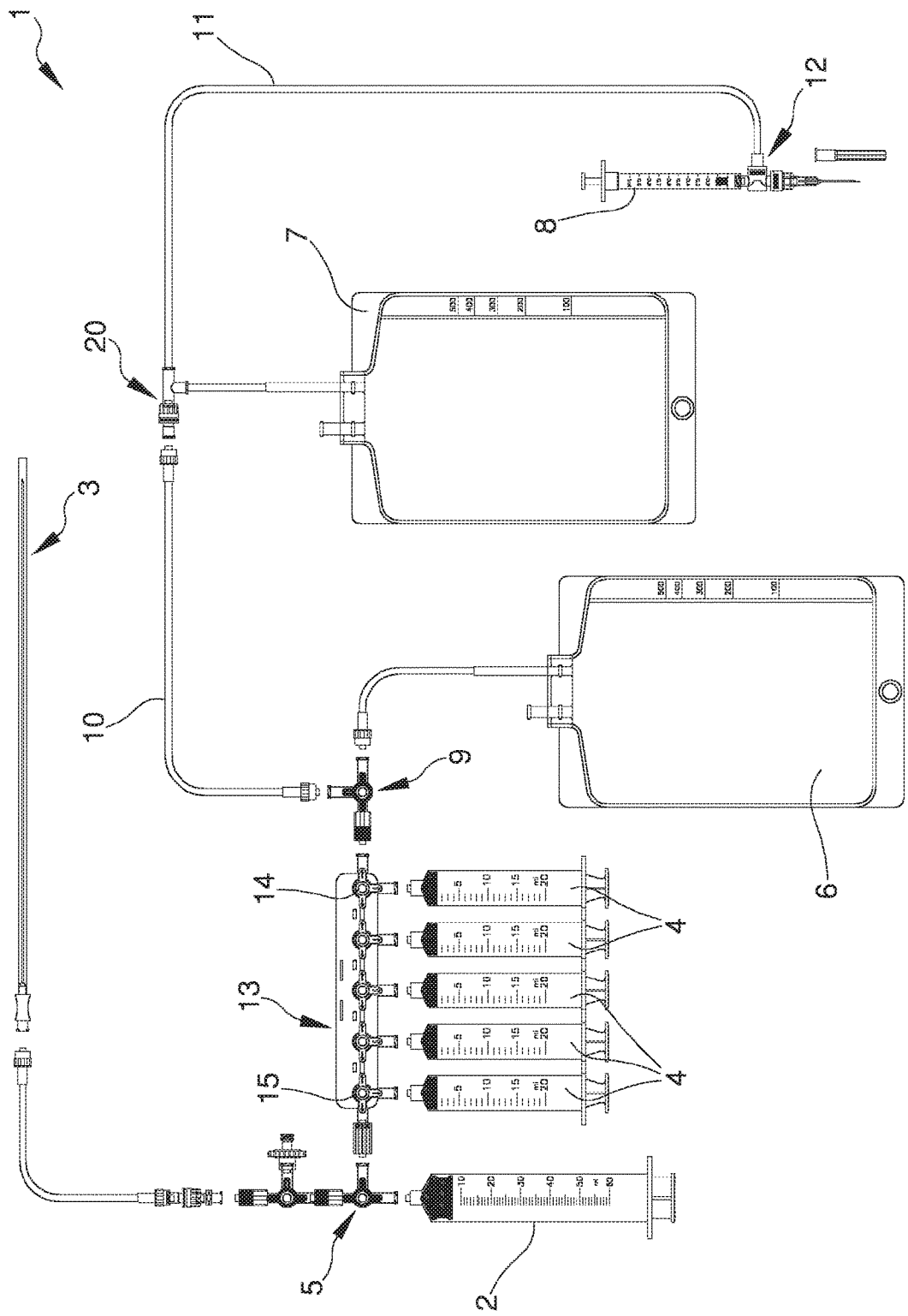

SYSTEM AND METHOD TO DIVIDE LIPOSUCTION FAT INTO ALIQUOTS

RELATED APPLICATIONS

This application is a National Phase of PCT Patent Application No. PCT/IB2014/063634 having International filing date of Aug. 1, 2014, which claims the benefit of priority of Italian Patent Application No. MO2013A000227 filed on Aug. 2, 2013. The contents of the above applications are all incorporated by reference as if fully set forth herein in their entirety.

FIELD AND BACKGROUND OF THE INVENTION

The present invention relates to a method and to a system to divide fat taken by means of liposuction into aliquots.

The fat removed by means of liposuction is known to be used for infiltrations for remodeling and/or regenerative purposes, especially in aesthetic medicine.

Currently, one of the most used liposuction procedures is the so-called "water-jet liposuction" during which the subcutaneous fat to be aspirated is affected by a jet of water under pressure so as to detach it from the surrounding tissues.

The aspirated fat, together with a share of water, is inserted into a container, which is then put under vacuum and sealed.

Currently, in order to perform the infiltrations, the container is opened and the doses of fat are taken by means of a syringe from time to time.

In practice, such a known procedure defines a system of taking and injection of open fat, i.e. not isolated from any possible contaminants, as well as unpractical to the doctor or health care professional who has to take and inject the doses of fat.

SUMMARY OF THE INVENTION

The main aim of the present invention is to provide a system and a method to divide liposuction fat into aliquots which allow to provide aliquots of fat prepared for infiltration.

Within this aim, one object of the invention is to provide a system and a method to divide liposuction fat into aliquots in which fat is always kept isolated from the outside environment up to and including its division into aliquots.

Another object of the present invention is to provide a system and a method to divide liposuction fat into aliquots which can overcome the mentioned drawbacks of the prior art in the ambit of a simple, rational, easy and effective to use as well as affordable solution.

The above mentioned objects are achieved by the present system to divide liposuction fat into aliquots according to claim 1.

BRIEF DESCRIPTION OF THE SEVERAL VIEWS OF THE DRAWINGS

Other characteristics and advantages of the present invention will become better evident from the description of a preferred, but not exclusive, embodiment of a system and a method to divide liposuction fat into aliquots, illustrated by way of an indicative, but not limitative, example in the accompanying drawings in which FIG. 1 is a schematic view of the system according to the invention.

DESCRIPTION OF SPECIFIC EMBODIMENTS OF THE INVENTION

With reference to this FIGURE, globally indicated by reference numeral 1 is a system to divide liposuction fat into aliquots.

The system 1 first comprises taking means 2, 3 to take from a container a quantity of adipose material, made available by means of liposuction, and to preserve sealed the quantity taken.

In this description, the term "adipose material" is used to refer to the material directly removed from a person with the process of liposuction, as it is.

Therefore, in the customary case of using water-jet liposuction, said material stored in the container substantially consists of human fat and an aqueous fluid that is substantially the water introduced by the doctor during liposuction.

Moreover, as known, the adipose material is contained under vacuum in the closed container.

The system 1 also comprises at least a separation syringe 4 (but preferably a plurality, for the reasons explained hereinafter) able to be put in communication with the taking means 2, 3, and able to contain at least a portion of the quantity of adipose material taken by the same.

The separation syringe 4 is provided so as to separate, by gravity, the fat from the aqueous fluids composing the adipose material of the portion contained in the syringe 4 itself, and is preferably arranged vertically.

In practice, it is known that fat is immiscible in water and also that fat and water have different specific weights.

The separation syringe 4 is suitably arranged vertical (i.e. arranged with its length vertical) or in any case not horizontal, so that water flows to the bottom of the same and therefore under the fat.

In detail, the separation syringe 4 is arranged with its containment barrel vertical, with the plunger on the top and with the so-called "beak" arranged below.

The invention also provides first connection means 5 to put in sealed communication the taking means 2, 3 with the separation syringe 4.

Preferably, the taking means comprise a taking syringe 2 connected to a taking needle 3 able to perforate the receptacles which contain adipose material under vacuum which preserve such material sealed and under vacuum.

In this case, the first connection means 5 may comprise first valve means placed between the taking syringe 2 and the taking needle 3 to put in communication alternately the needle 3 with the syringe 2 or the latter with the separation syringe 4; for example, such valve means may comprise at least a two or three-way cock 5.

Furthermore, the proposed system 1 comprises at least a rejection container 6 (e.g. a common drip bag), able to be put in communication with the separation syringe 4 so as to receive the separated aqueous fluids, following their ejection from the separation syringe 4 itself (as will be explained in detail when describing the operation of the invention).

The invention further comprises at least a syringe device 7, 8 able to be put in communication with the separation syringe 4 so as to receive an aliquot of fat, following its ejection from the separation syringe 4 itself, which device 7, 8 is able, alternately, to contain sealed or to inject fat for the infiltrations.

Moreover, second connection means 9 are provided (preferably comprising a two- or three-way cock) able to put in sealed communication, and alternately, the separation syringe 4 and the rejection container 6 or the separation syringe 4 and the syringe device 7, 8.

The syringe device 7, 8 comprises a receptacle 7, such as a drip bag, connected sealed to an infiltration syringe 8.

More particularly, the receptacle 7 is connected sealed to an infiltration syringe 8, e.g. through a second channel 11. Preferably, the syringe 8 comprises a single-acting valve 12. It should be noticed that the single-acting valve 12 may be arranged at the outlet of the barrel of the infiltration syringe 8.

The syringe device 7, 8 has attachment means 20, e.g. of the Luer-lock connector type, connectable in a removable manner to the second connection means 9, to define, as a result of their filling with fat, a portable unit to contain (in isolation), and to inject an aliquot of fat (i.e. a "kit for infiltrations" as will be detailed in a later section). In the preferred embodiment shown in the illustrations, between the attachment means 20 and the second connection means 9 is positioned a branch-off channel 10 having in turn Luer-lock type connections both to the attachment means 20 and to the second connection means 9.

Before explaining the operation of the invention, it is specified that, the one described above, is a completely closed system 1, that is to say that, even if it includes separable sub-units, it has been devised to contain sealed the adipose material and the fat contained and processed in it, without allowing them to come into contact with any contaminants, including air of the surrounding environment.

The system 1 of the invention operates as explained below.

The doctor or health care professional perforates the receptacle containing the liposuction adipose material using the needle 3 of the taking means, and aspirates the material by means of the syringe 2, taking care to prepare the cock 5, placed between them, in the configuration allowing the communication between needle 3 and syringe 2.

At this point, the adipose material, which includes water and fat, is contained within the taking syringe 2.

The user operates the cock 5 of the first connection means so as to put in communication the taking syringe 2 with the separation syringe 4.

As mentioned before, preferably, a plurality of separation syringes 4, e.g. five, are connected in parallel by means of third valve means 13, in turn connected in series to said first and second connection means 5, 9, downstream of the former and upstream of the latter.

This is because as many separation syringes 4 are present in the system 1, the faster is the separation operation thereof.

The third valve means (which may be a ramp 13 of three-way cocks as in FIG. 1) are able to alternately allow the entry of respective portions of said quantity of adipose material, and the outflow of fat following its separation from said fluids.

In this stage, each cock of the third connection means 13 is operated so as to allow the passage from the cock 5 of the first communication means to the respective syringe 4 and to the upstream and downstream cocks in the ramp 13; the last downstream cock 14 in the ramp 13 is instead arranged in its configuration wherein it only allows the communication between the upstream cock and the respective syringe 4.

At this point, the adipose material is pushed out the taking syringe 2 and aspirated within the separation syringes 4, all arranged vertical, e.g. side by side, within which the material is left for a time between fifteen and thirty minutes, during which the above separation occurs.

Thereafter, the cocks of ramp 13 are operated in a configuration wherein they allow the communication between the respective syringe 4 and the downstream and upstream cocks, with the first upstream cock 15 which is in a configuration wherein its communication is blocked with cock 5 of the first connection means, while the last downstream cock 14 is in the configuration wherein all its ways are open; at the same time, the cock 9 of the second connection means is controlled so as to be arranged in the configuration wherein it only allows the communication between the ramp 13 of the third communication means and the rejection container 6.

Then, the syringes 4 are operated, one at a time and in succession, so as to eject water, which therefore flows into the rejection container 6, which can be connected to the cock 9 of the second connection means via a Luer-lock connector, and therefore can be replaced with another empty container.

At this point, the separation syringes 4 are operated, one at a time, starting from the syringe most upstream to the most downstream one in order to transfer the fat contained in them within the cocks of the ramp 13, filling them.

Then, the cock 9 of the second connection means is controlled to connect the ramp 13 with the syringe device 7, 8 (optionally with the interposition of the above branch-off channel 10) and the plungers of the separation syringes 4 are pressed to transfer the share of fat within the receptacle 7 and the infiltration syringe 8 which, as said, are preferably devised so as to make up an independent and portable kit for infiltration, once filled with fat.

Then, such a kit can be detached for its replacement with another syringe device, for the purposes of its filling.

Optionally, several syringe devices can be connected in parallel downstream of the separation syringes 4 and of the relative ramp 13 (e.g. by providing that the second connection means 9 include a plurality of respective cocks or valve means with multiple ways, etc.) so as to define a plurality of kits of infiltration at a time.

In this case, the separation syringe, or the set of separation syringes 4, includes more than one aliquot, i.e., an aliquot for each kit.

Moreover, in principle, in the event of the first connection means 5 comprising a plurality of cocks such as the one described above, or different valve means with multiple ways, several series of separation syringes may be arranged in parallel, with the relative ramps, etc.

The system 1 described above implements the method to divide into aliquots the fat removed from a person by means of liposuction, in order to make a subsequent infiltration, which comprises the following steps:

providing a closed receptacle, in which adipose material removed by means of liposuction is contained under vacuum;

perforating said receptacle and taking from it a quantity of adipose material, while keeping the latter isolated from contaminants;

separating fat from aqueous fluids composing the adipose material of said taken quantity, so as to define at least an aliquot of fat; and making available said aliquot, keeping it isolated from contaminants, until it is used to make infiltrations.

Preferably, as already explained in the description of the system, the method of the invention provides that the separation between fat and aqueous fluids (which are essentially made of water, for the reasons already explained) occurs by placing the adipose material they make up in a vertical container 4, where said fat and said fluids, having different specific weights, separate from one another due to the action of the force of gravity.

In practice it has been found how the described invention achieves the intended objects and in particular the fact is underlined that it provides a closed system 1 for the division of fat into aliquots, which prepares pre-filled kits for infiltration.

What is claimed is:

1. System to divide liposuction fat into aliquots, said system comprising an adipose material container containing a quantity of adipose material made available by liposuction, wherein said system also comprises:
    at least one separation syringe in communication with said adipose material container, each said at least one separation syringe configured to contain at least a portion of said quantity and to separate, by gravity, the fat in the adipose material from the aqueous fluids in the adipose material;
    a first valve configured to provide communication between said adipose material container and said at least one separation syringe;
    at least one rejection container, in communication with said at least one separation syringe, said at least one rejection container configured to receive said aqueous fluids, following their ejection from said at least one separation syringe;
    at least one infiltration container in communication with said at least one separation syringe so as to receive an aliquot of fat, following its ejection from said separation syringe; and
    a second valve configured to provide communication alternately between said at least one separation syringe and said at least one rejection container or between said at least one separation syringe and said at least one infiltration container,
    where said at least one infiltration container comprises at least a receptacle and at least one infiltration syringe connected to one another, wherein said at least one infiltration container is connectable in a removable manner to said second valve to define a portable unit to contain and to inject an aliquot of fat.

2. A system according to claim 1, wherein said at least one infiltration container comprises an attachment connectable in a removable manner to said second valve.

3. A system according to claim 1, wherein said receptacle is connected to said infiltration syringe through a second channel.

4. A system according to claim 1, wherein said infiltration syringe comprises at least one single-acting valve configured to prevent the fat contained in the infiltration syringe from flowing out towards said receptacle.

5. A system according to claim 2, wherein said system further comprises a branch-off channel to connect said at least one infiltration container to said second valve, said branch-off channel being positioned between said attachment and said second valve.

6. A system according to claim 1, wherein said adipose material container comprises a taking syringe connected to a taking needle able to perforate adipose material receptacles.

7. A system according to claim 6, wherein said first valve is disposed between said syringe and said needle and is configured to provide communication alternately between said needle and said taking syringe or between said taking syringe and said at least one separation syringe.

8. A system according to claim 1, wherein said at least one separation syringe comprises a plurality of separation syringes connected to one another in parallel by a plurality of third valves in turn connected in series to said first valve and said second valve, downstream of the former and upstream of the latter, said third valves configured to alternately allow entry of portions of said quantity of adipose material, and the outflow of aqueous fluid, following its separation from said fat.

9. A system according to claim 1, wherein said second valve comprises at least one two-way cock.

10. A system according to claim 7, wherein said third valves comprise a sequence of three-way cocks.

* * * * *